US012736882B2

(12) United States Patent
Su et al.

(10) Patent No.: US 12,736,882 B2
(45) Date of Patent: Sep. 15, 2026

(54) POLYMER CROSSLINK DE-CROSSLINK PROCESSES FOR RESIST PATTERNING

(71) Applicant: Taiwan Semiconductor Manufacturing Co., Ltd., Hsinchu (TW)

(72) Inventors: Yu-Chung Su, Hsinchu (TW); Lilin Chang, Hsinchu (TW); Jia-Lin Wei, Hsinchu (TW); Ching-Yu Chang, Hsinchu (TW)

(73) Assignee: TAIWAN SEMICONDUCTOR MANUFACTURING COMPANY, LTD., Hsinchu (TW)

( * ) Notice: Subject to any disclaimer, the term of this patent is extended or adjusted under 35 U.S.C. 154(b) by 510 days.

(21) Appl. No.: 17/734,975

(22) Filed: May 2, 2022

(65) Prior Publication Data

US 2023/0350302 A1 Nov. 2, 2023

(51) Int. Cl.

| | |
|---|---|
| ***G03F 7/30*** | (2006.01) |
| ***C07C 55/00*** | (2006.01) |
| ***C08L 23/04*** | (2006.01) |
| ***C08L 101/08*** | (2006.01) |
| ***G03F 7/038*** | (2006.01) |
| ***G03F 7/039*** | (2006.01) |
| ***G03F 7/09*** | (2006.01) |
| ***G03F 7/16*** | (2006.01) |

(Continued)

(52) U.S. Cl.

CPC ................ *G03F 7/30* (2013.01); *C07C 55/00* (2013.01); *C08L 23/04* (2013.01); *C08L 101/08* (2013.01); *G03F 7/038* (2013.01); *G03F 7/0382* (2013.01); *G03F 7/039* (2013.01); *G03F 7/092* (2013.01); *G03F 7/168* (2013.01); *G03F 7/26* (2013.01); *H10P 50/73* (2026.01)

(58) Field of Classification Search

CPC . G03F 7/30; G03F 7/092; G03F 7/038; G03F 7/0382

See application file for complete search history.

(56) References Cited

U.S. PATENT DOCUMENTS

| | | | | |
|---|---|---|---|---|
| 6,027,854 A * | 2/2000 | Nishi | G03F 7/0045 | 430/326 |
| 2001/0035394 A1 * | 11/2001 | Takeda | G03F 7/0045 | 216/41 |

(Continued)

FOREIGN PATENT DOCUMENTS

| | | | |
|---|---|---|---|
| TW | 202111434 A | 3/2021 | |
| TW | I722631 B | 3/2021 | |
| TW | 202116834 A * | 5/2021 | C08F 2/48 |

*Primary Examiner* — John S. Chu

(74) *Attorney, Agent, or Firm* — Seed Intellectual Property Law Group LLP

(57) ABSTRACT

A method for forming a semiconductor structure is provided. The method includes forming a photoresist layer over a substrate. The photoresist layer includes a polymer, a photoacid initiator and a crosslinker containing at least two crosslinking sites. The photoresist layer is then cured to crosslink the polymer, thereby forming a crosslinked polymer. Next, the photoresist layer is exposed to a radiation. An acid produced from exposure of the photoacid generator de-crosslinks the crosslinked polymer in exposed portions of the photoresist layer. The exposed portions of the photoresist layer are subsequently removed to form a patterned photoresist layer.

20 Claims, 8 Drawing Sheets

(51) Int. Cl.

| | |
|---|---|
| ***G03F 7/26*** | (2006.01) |
| ***H10P 50/00*** | (2026.01) |

(56) References Cited

U.S. PATENT DOCUMENTS

| | | | | |
|---|---|---|---|---|
| 2002/0001770 | A1* | 1/2002 | Cameron | G03F 7/0045 430/326 |
| 2002/0076643 | A1* | 6/2002 | Ohsawa | G03F 7/0045 430/311 |
| 2015/0147697 | A1* | 5/2015 | Hatakeyama | G03F 7/2037 430/326 |
| 2016/0054652 | A1* | 2/2016 | Hatakeyama | G03F 7/2004 430/296 |
| 2017/0153549 | A1* | 6/2017 | Shibayama | C09D 183/04 |
| 2017/0260315 | A1* | 9/2017 | Imada | G03F 7/0236 |
| 2019/0056657 | A1* | 2/2019 | Toida | C07C 39/367 |
| 2019/0354013 | A1* | 11/2019 | Maruyama | H10F 39/804 |

* cited by examiner

POLYMER CROSSLINK DE-CROSSLINK PROCESSES FOR RESIST PATTERNING

BACKGROUND

The semiconductor integrated circuit (IC) industry has experienced exponential growth. Technological advances in IC materials and design have produced generations of ICs where each generation has smaller and more complex circuits than the previous generation. In the course of IC evolution, functional density (i.e., the number of interconnected devices per chip area) has generally increased while geometry size (i.e., the smallest component (or line) that can be created using a fabrication process) has decreased. This scaling down process generally provides benefits by increasing production efficiency and lowering associated costs. Such scaling down has also increased the complexity of processing and manufacturing ICs.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
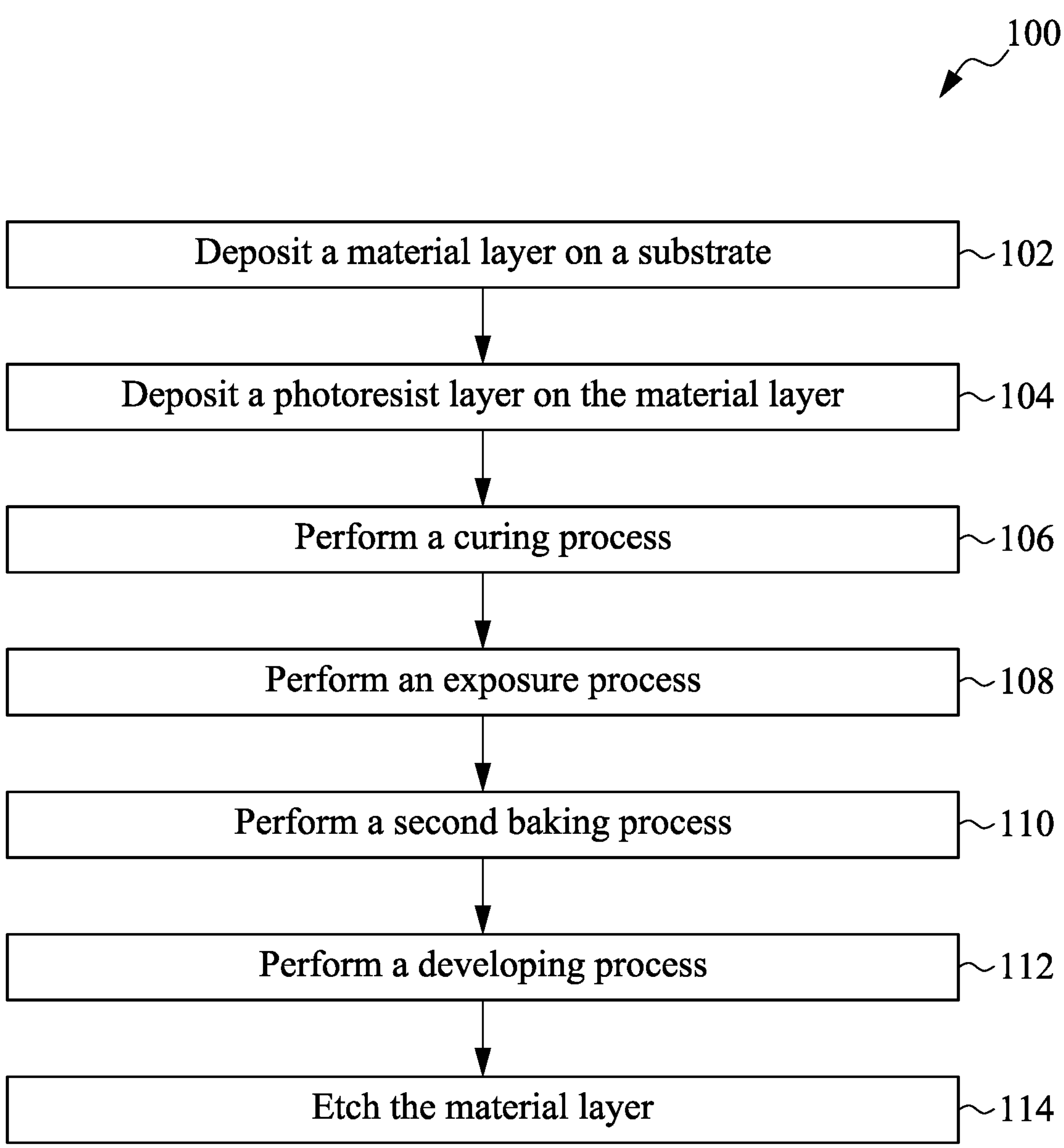
FIG. 1 is a flow chart of a method for fabricating a semiconductor device, in accordance with some embodiments.

The following disclosure provides many different embodiments, or examples, for implementing different features of the provided subject matter. Specific examples of components, values, operations, materials, arrangements, or the like, are described below to simplify the present disclosure. These are, of course, merely examples and are not intended to be limiting. Other components, values, operations, materials, arrangements, or the like, are contemplated. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. System may be otherwise oriented (rotated 90 degrees or at other orientations) and the spatially relative descriptors used herein may likewise be interpreted accordingly.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkylene" is a divalent or multivalent cycloalkyl, which typically connects one portion of a molecule to a radical group or connects two or more radical groups. Unless otherwise stated specifically in the specification, a cycloalkyl (or cycloalkylene) group is optionally substituted.

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkylene" refers to an alkylene group, as defined above, comprising at least one heteroatom (e.g., N, O, P or S) within the alkylene chain or at a terminus of the alkylene chain. In some embodiments, the heteroatom is within the alkylene chain (i.e., the heteroalkylene comprises at least one carbon-heteroatom-carbon bond). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted.

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cyclocalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e., thienyl). Unless stated otherwise specifically in the specification, a heteroaryl group is optionally substituted.

The term "substituted" used herein means any of the above groups (e.g., alkyl, alkylene, alkylamino, alkylaminoalkyl, alkoxy, aryl, arylene, carbocyclyl, cycloalkyl, cycloalkylene, cycloheteroalkylene, haloalkyl, haloalkylene, haloheteroalkylene, heteroalkylene, heterocyclyl, heteroaryl and/or heteroarylene) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles.

For example, "substituted" includes any of the above groups in which one or more hydrogen atoms are replaced with $—NR_gR_h$, $—NR_gC(═O)R_h$$—NR_gC(═O)R_h$, $—NR_gC(═O)NR_gR_h$, $—NR_gC(═O)OR_h$, $—NR_gSO_2R_h$, $—OC(═O)NR_gR_h$, $—OR_g$, $—SR_g$, $—SOR_g$, $—SO_2R_g$, $—OSO_2R_g$, $—SO_2OR_g$, $═NSO_2R_g$, and $—SO_2NR_gR_h$. "Substituted" also means any of the above groups in which one or more hydrogen atoms are replaced with $—C(═O)R_g$, $—C(═O)OR_g$, $—C(═O)NR_gR_h$, $—CH_2SO_2R_g$, $—CH_2SO_2NR_gR_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

IC fabrication uses one or more photolithography processes to transfer geometric patterns to a film or substrate. Geometric shapes and patterns on a semiconductor make up the complex structures that allow the dopants, electrical properties and wires to complete a circuit and fulfill a technological purpose. In a photolithography process, a photoresist is applied as a thin film to a substrate, and subsequently exposed to one or more types of radiation or light through a photomask. The photomask contains clear and opaque features that define a pattern which is to be created in the photoresist layer. Areas in the photoresist exposed to light transmitted through the photomask are made either soluble or insoluble in a specific type of solution known as a developer. In the case when the exposed areas are soluble, a positive image of the photomask is produced in the photoresist and this type of photoresist is called a positive photoresist. On the other hand, if the unexposed areas are dissolved by the developer, a negative image results in the photoresist and this type of photoresist is called a negative photoresist. The developer removes the more soluble areas, leaving the patterned photoresist in place. The resist pattern is then used as an etch mask in subsequent etching processes, transferring the pattern to an underlying material layer, thereby replicating the mask pattern in the underlying material layer. Alternatively, the resist pattern is then used as an ion implantation mask in subsequent ion implantation processes applied to the underlying material layer, such as an epitaxial semiconductor layer.

The quality of the resist pattern directly impacts the quality of the final ICs. As the scaling down process continues, pattern collapse is becoming an emerging problem due to the high aspect ratios of the resist features. During the developing process, the smaller dimension of the resist features greatly increases capillary force of the developer and/or rinse solution, which leads to the collapse of the resist features. The resist top loss also becomes more serious as the dimension shrinks because the smaller resist features diffract more light.

In embodiments of the present disclosure, photolithography processes utilizing photoresist capable of both crosslink and de-crosslink are provided to reduce the defects generated during the patterning process. The photoresist crosslinking process increases the mechanical strength and solvent resistance of the photoresist, making the photoresist less prone to collapse during the developing process. The photoresist de-crosslink process de-crosslinks the crosslinked photoresist so that the photoresist can be removed by a developer. As a result, the quality of the resist pattern is improved, which helps to improve the yield and the relativity of the device.

FIG. 1 is a flowchart illustrating a method 100 of fabricating a semiconductor structure 200, in accordance with some embodiments of the present disclosure. FIGS. 2A through 2G are cross-sectional views of a semiconductor structure 200 at various fabrication stages in accordance with some embodiments of the present disclosure. The method 100 is described below in conjunction with FIG. 1 and FIGS. 2A through 2G where the semiconductor structure 200 is fabricated by using embodiments of the method 100. It is understood that additional steps can be provided before, during, and after the method 100, and some of the steps described below can be replaced or eliminated, for additional embodiments of the method. It is further understood that additional features can be added in the semiconductor structure 200, and some of the features described below can be replaced or eliminated, for additional embodiments of the semiconductor structure 200.

The semiconductor structure 200 may be an intermediate structure during the fabrication of an IC, or a portion thereof. The IC may include logic circuits, memory structures, passive components (such as resistors, capacitors, and inductors), and active components such as diodes, field-effect transistors (FETs), metal-oxide semiconductor field effect transistors (MOSFETs), complementary metal-oxide semiconductor (CMOS) transistors, bipolar transistors, high voltage transistors, high frequency transistors, fin-like FETs (FinFETs), other three-dimensional (3D) FETs, and combinations thereof. The semiconductor structure 200 may include a plurality of semiconductor devices (e.g., transistors), which may be interconnected.

Figure 2A:
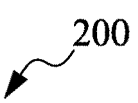
FIGS. 2A-2G are cross-sectional views of a semiconductor structure fabricated using the method of FIG. 1, in accordance with some embodiments.
Figure 2A:
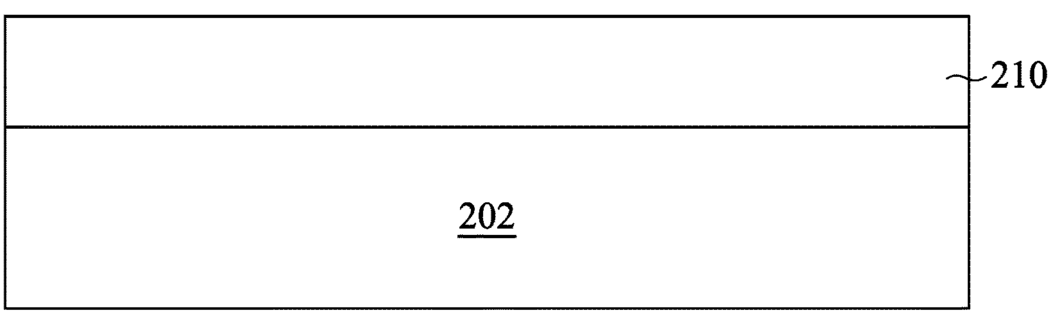

Referring to FIGS. 1 and 2A, the method 100 includes operation 102, in which a material layer 210 is deposited on a substrate 202, in accordance with some embodiments. FIG. 2A is a cross-sectional view of a semiconductor structure 200 after depositing the material layer 210 on the substrate 202, in accordance with some embodiments.

In some embodiments, the substrate 202 may be a bulk semiconductor substrate including one or more semiconductor materials. In some embodiments, the substrate 202 may include silicon, silicon germanium, carbon doped silicon (Si:C), silicon germanium carbide, or other suitable semiconductor materials. In some embodiments, the substrate 202 is composed entirely of silicon.

In some embodiments, the substrate 202 may include one or more epitaxial layers formed on a top surface of a bulk semiconductor substrate. In some embodiments, the one or more epitaxial layers introduce strains in the substrate 202 for performance enhancement. For example, the epitaxial layer includes a semiconductor material different from that of the bulk semiconductor substrate, such as a layer of silicon germanium overlying bulk silicon or a layer of silicon overlying bulk silicon geranium. In some embodiments, the epitaxial layer(s) incorporated in the substrate 202 are formed by selective epitaxial growth, such as metalorganic vapor phase epitaxy (MOVPE), molecular beam epitaxy (MBE), hydride vapor phase epitaxy (HVPE), liquid phase epitaxy (LPE), metal-organic molecular beam epitaxy (MOMBE), or combinations thereof.

In some embodiments, the substrate 202 may be a semiconductor-on-insulator (SOI) substrate. In some embodiments, the SOI substrate includes a semiconductor layer, such as a silicon layer formed on an insulator layer. In some embodiments, the insulator layer is a buried oxide (BOX) layer including silicon oxide or silicon germanium oxide. The insulator layer is provided on a handle substrate, such as a silicon substrate. In some embodiments, the SOI substrate is formed using separation by implanted oxygen (SIMOX) or other suitable technique, such as wafer bonding and grinding.

In some embodiments, the substrate 202 may also include a dielectric substrate such as silicon oxide, silicon nitride, silicon oxynitride, a low-k dielectric, silicon carbide, and/or other suitable layers.

In some embodiments, the substrate 202 may also include various p-type doped regions and/or n-type doped regions, implemented by a process such as ion implantation and/or diffusion. Those doped regions include n-well, p-well, lightly doped region (LDD) and various channel doping profiles configured to form various IC devices, such as a COMOS transistor, imaging sensor, and/or light emitting diode (LED). The substrate 202 may further include other functional features such as a resistor and/or a capacitor formed in and/or on the substrate 202.

In some embodiments, the substrate 202 may also include various isolation features. The isolation features separate various device regions in the substrate 202. The isolation features include different structures formed by using different processing technologies. For example, the isolation features may include shallow trench isolation (STI) features. The formation of an STI may include etching a trench in the substrate 202 and filling in the trench with insulator materials such as silicon oxide, silicon nitride, and/or silicon oxynitride. The filled trench may have a multi-layer structure such as a thermal oxide liner layer with silicon nitride filling the trench. A chemical mechanical polishing (CMP) may be performed to polish back excessive insulator materials and planarize the top surface of the isolation features.

In some embodiments, the substrate 202 may also include gate stacks formed by dielectric layers and electrode layers. The dielectric layers may include an interfacial layer and a high-k dielectric layer deposited by suitable techniques, such as chemical vapor deposition (CVD), atomic layer deposition (ALD), physical vapor deposition (PVD), thermal oxidation, combinations thereof, and/or other suitable techniques. The interfacial layer may include silicon dioxide and the high-k dielectric layer may include LaO, AlO, ZrO, TiO, $Ta_2O_5$, $Y_2O_3$, $SrTiO_3$, $BaTiO_3$, BaZrO, HfZrO, HfLaO, HfSiO, LaSiO, AlSiO, HfTaO, HfSiO, $(Ba,Sr)TiO_3$ (BST), $Al_2O_3$, $Si_3N_4$, SiON, and/or other suitable materials. The electrode layer may include a single layer or alternatively a multi-layer structure, such as various combinations of a metal layer with a work function to enhance the device performance (work function metal layer), liner layer, wetting layer, adhesion layer and a conductive layer of metal, metal alloy or metal silicide). The electrode layer may include Ti, Ag, Al, TiAlN, TaC, TaCN, TaSiN, Mn, Zr, TiN, TaN, Ru, Mo, Al, WN, Cu, W, any suitable materials, and/or a combination thereof.

In some embodiments, the substrate 202 may also include a plurality of inter-level dielectric (ILD) layers and conductive features integrated to form an interconnect structure configured to couple the various p-type and n-type doped regions and the other functional features (such as gate electrodes), resulting in a functional integrated circuit. In one example, the substrate 202 may include a portion of the interconnect structure and the interconnect structure may include a multi-layer interconnect (MLI) structure and an ILD layer integrated with an MLI structure, providing an electrical routing to couple various devices in the substrate 202 to the input/output power and signals. The interconnect structure includes various metal lines, contacts and via features (or via plugs). The metal lines provide horizontal electrical routing. The contacts provide vertical connection between silicon substrate and metal lines while via features provide vertical connection between metal lines in different metal layers.

The material layer 210 is disposed on the substrate 202. The material layer 210 is a layer to be processed by the method 100, such as to be patterned or to be implanted. In some embodiments, the material layer 210 is a hardmask layer to be patterned. In some embodiments, the material layer 210 includes a dielectric material such as silicon oxide, silicon nitride, or silicon oxynitride. In some other embodiments, the material layer 210 includes a metal oxide such as titanium oxide or a metal nitride such as titanium nitride. In some embodiments, the material layer 210 also serves as an anti-reflection coating (ARC) layer whose composition is chosen to minimize reflectivity of radiation implemented during exposure of the photoresist layer 220. For example, in some embodiments, the material layer 210 includes silicon oxide, silicon oxygen carbide, or plasma enhanced chemical vapor deposited silicon oxide. The material layer 210 may be formed by any suitable process including chemical vapor deposition (CVD), physical vapor deposition (PVD), plasma enhanced chemical vapor deposition (PECVD), atomic layer deposition (ALD), or spin coating, and may be formed to any suitable thickness.

Figure 2B:
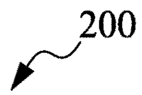
Figure 2B:
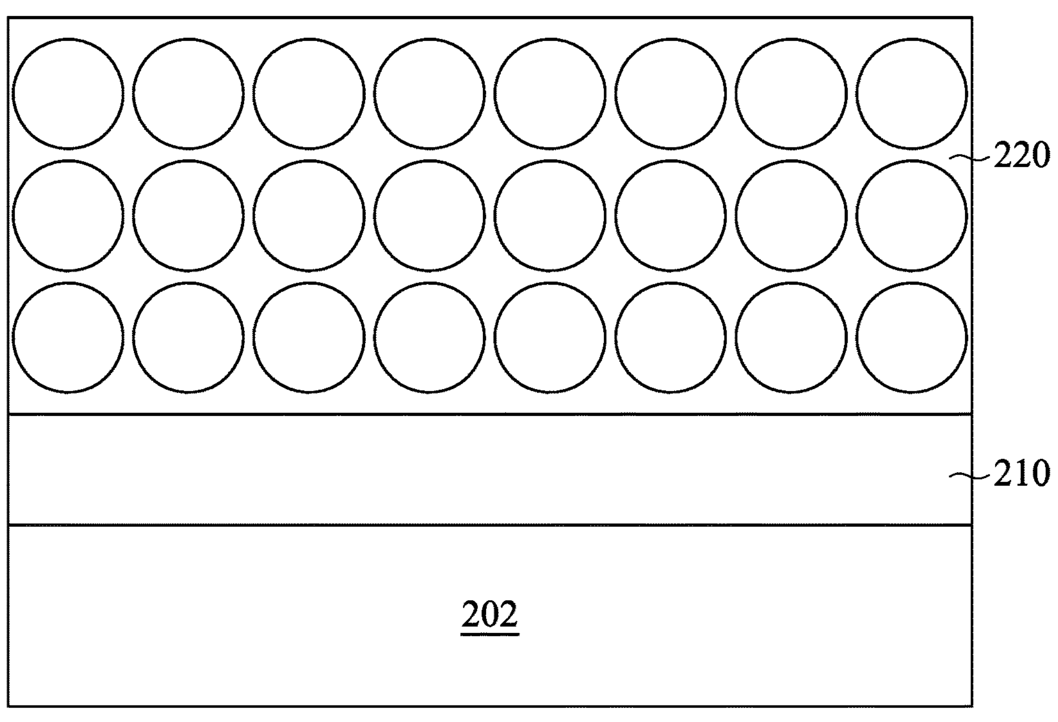

Referring to FIGS. 1 and 2B, the method 100 proceeds to operation 104, in which a photoresist layer 220 is deposited on the material layer 210, in accordance with some embodiments. FIG. 2B is a cross-sectional view of a semiconductor structure 200 after depositing the photoresist layer 220 on the material layer 210, in accordance with some embodiments.

The photoresist layer 220 is sensitive to a radiation such as a DUV radiation (e.g., 248 nm radiation from a KrF laser or 193 nm radiation from an ArF laser), an EUV radiation (e.g., 13.5 nm radiation), an electron beam (e-beam), or an ion beam. In the present embodiment, the photoresist layer 220 is sensitive to the EUV radiation and is used in an EUV lithography process.

In some embodiments, the photoresist layer 220 includes a polymer, a catalyst, and a crosslinker.

The polymer may have an average molecular weight from about 1,000 Daltons to 1000,000 Daltons, for example, from about 1,000 Daltons to 25,000 Daltons. Examples of polymers include polyacrylates, polymethacrylates, poly(hydroxy styrene) (PHS), polyesters, polycarbonates, polyamic acids, poly(styrene)-co-maleic anhydride (COMA), mixtures thereof, and copolymers thereof.

The polymer includes a reactive group attached to the polymer backbone. The reactive group is capable of reacting to the crosslinker, and thus provides a crosslinking site. In some embodiments, the reactive group may include a hydroxyl group, an alkoxy group, an amine group, a thiol group, an ester group, an alkene group, an alkyne group, an epoxy group, an aziridine group, an oxetane group, an aldehyde group, a ketone group, or a carboxylic acid group. In some embodiments, the polymer comprises a carboxylic acid group.

The polymer may also comprise other groups attached to the polymer backbone that help to improve a variety of properties of the polymer. For example, in some embodiments, the polymer may also include a light-sensitive functional group bonded to the polymer backbone. During the exposure process, the light-sensitive functional group may help to improve the photon absorption efficiency. The light-sensitive functional group is selected based upon the wavelength at which the photoresist layer 220 will be irradiated. For example, at wavelengths of 248 nm, suitable light-sensitive functional groups include naphthalenes (e.g., napthitholic acid methacrylate, 3,7-dihydroxynaphthoic acid), heterocyclic chromophores, carbazoles, antiracenes (e.g., 9-anthracene methyl methacrylate, 9-anthraceniecarboxylic acid), and functional moieties of the foregoing. At wavelengths of 193 nm, suitable light-sensitive functional groups include substituted and unsubstituted phenyls, heterocyclic chromophores (e.g., furan rings, thiophene rings), and functional moieties of the foregoing.

The catalyst is an acid generator. In some embodiments, the acid generator is a photoacid generator that is capable of releasing or generating an acid in the presence of light. Photoacid generators may include a sulfonium cation, such as a triphenylsulfonium (TPS) group; and an anion, such as a triflate anion. Examples of photoacid generators include triphenyl sulfonium nonaflate (TPSN), α-(trifluoro-methylsulfonyloxy)-bicyclo[2.2.1]hept-5-ene-2, 3-dicarb-o-ximide (MDT), N-hydroxy-naphthalimide dodecane sulfonate (DDSN), benzoin tosylate, t-butylphenyl-α-(p-toluenesulfonyloxy)-acetate and t-butyl-α-(p-toluenesulfonyloxy)-acetate, triarylsulfonium hexafluoroantimonate, diaryliodonium hexafluoroantimonate, hexafluoroarsenates, trifluoromethanesulfonates, iodonium perfluorooctanesulfonate, N-camphorsulfonyloxynaphthalimide, N-pentafluorophenylsulfonyloxynaphthalimide, ionic iodonium sulfonates such as diaryl iodonium (alkyl or aryl) sulfonate and bis-(di-t-butylphenyl) iodonium camphanylsulfonate, perfluoroalkanesulfonates such perfluoropentanesulfonate, perfluorooctane sulfonate, perfluoromethanesulfonate, aryl (e.g., phenyl or benzyl) triflates such as triphenylsulfonium triflate or bis-(t-butylphenyl) iodonium triflate; pyrogallol derivatives (e.g., trimesylate of pyrogallol), trifluoromethanesulfonate esters of hydroxyimides, α,α'-bis-sulfonyl-diazomethanes, sulfonate esters of nitro-substituted benzyl alcohols, naphthoquinone-4-diazides, alkyl disulfones, or the like.

The photoresist layer 220 may include from about 0.1% to 10% by weight of catalyst based upon the total weight of the polymer taken as 100% by weight. In some embodiments, the photoresist layer 220 includes from about 1% to about 5% by weight of catalyst.

The crosslinker functions to both crosslink and de-crosslink upon proper conditions. The crosslinker includes crosslinkable functional groups that are capable of reacting with the reactive group of polymer under thermal, radiation and weak acidic conditions to crosslink the polymers. The crosslinker also includes a cleavable linker that can be cleaved under an acidic condition to de-crosslink the crosslinked polymer. In some embodiments, the crosslinker has a structure of Formula (I):

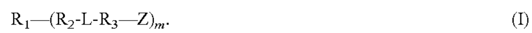

$$R_1—(R_2\text{-}L\text{-}R_3—Z)_m. \quad (I)$$

In Formula (I), $R_1$ is a core group. $R_1$ may include alkylene, haloalkylene, cycloalkylene, heteroalkylene, haloheteroalkylene, cycloheteroalkylene, arylene, haloarylene, or haloheteroarylene.

$R_2$ and $R_3$ are optional spacer groups. In some embodiments, $R_2$ and $R_3$ may be the same or different, and may independently be alkylene, haloalkylene, cycloalkylene, heteroalkylene, haloheteroalkylene, cycloheteroalkylene, arylene, haloarylene, or haloheteroarylene.

L is an optional cleavable linker. In some embodiments, the cleavable linker (L) is an acid cleavable linker which is stable under neutral and basic conditions, but is capable of being cleaved under an acidic condition such as at pH 1-3. Accordingly, the acid generated by the photoacid generator during the exposure to actinic radiation cleaves the cleavable linker (L), causing the de-crosslink of the crosslinked polymer. In some embodiments, the cleavable linker (L) may be selected from the group consisting of an ester group, a silyl ether group, an acetal group, a ketal group, an amide group, an imine group, an imide group, and a carbamate group.

Z is a crosslinkable functional group. In some embodiments, the crosslinkable functional group may be an ultraviolet (UV) curable group which can be crosslinked by UV curing. In some other embodiments, the crosslinking group may be a thermal crosslinkable group which can be crosslinked under an elevated temperature. In still some embodiments, the crosslinking group may be an acid crosslinkable group which can be crosslinked under a weak acidic condition. As used herein, the term "weak acid" means an acid that has a pKa in the range of 4-6. In some embodiments, the crosslinkable group functional group (Z) may be selected from the group consisting of a halide group, a hydroxyl group, an alkoxy group, an amine group, a thiol group, an ester group, an alkene group, an alkyne group, an epoxy group, an aziridine group, an oxetane group, an aldehyde group, a ketone group, a vinyl ether group, a sulfonate group, and a carboxylic acid group.

The crosslinker contains two or more crosslinkable functional groups. In some embodiments, the crosslinker contains two crosslinkable functional groups. In some embodiments, the crosslinker contains three crosslinkable functional groups. In some embodiments, the crosslinker contains four crosslinkable functional groups. Accordingly, in Formula (I), m is an integer greater than 1. In some embodiments, m is 2, 3 or 4.

In some embodiments, the crosslinker has one of the following structures:

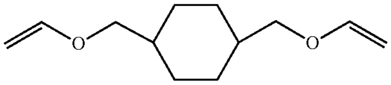
,

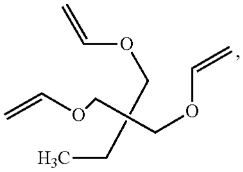
,

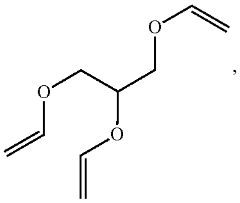
,

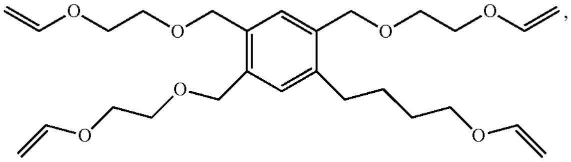
,

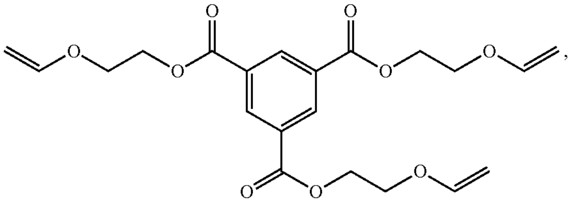
,

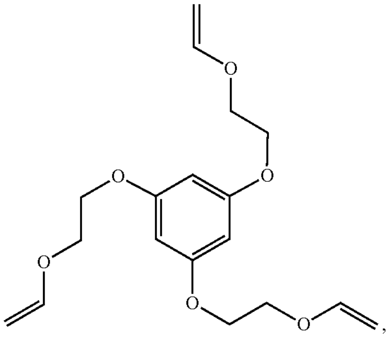
,

-continued

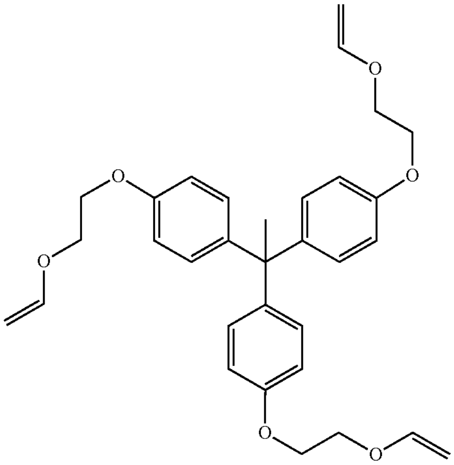
,

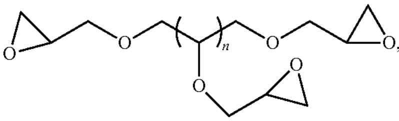
,

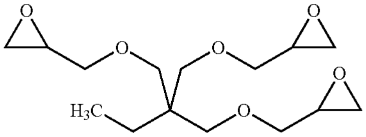
,

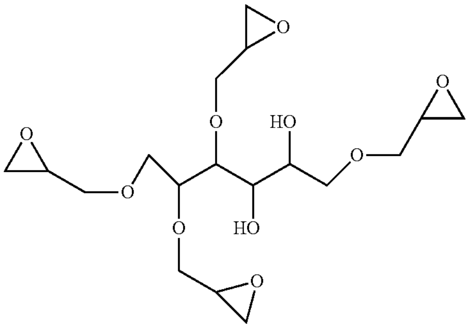
,

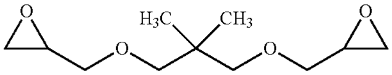
,

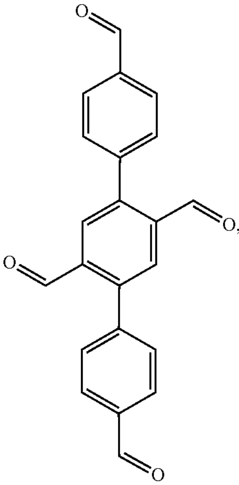
,

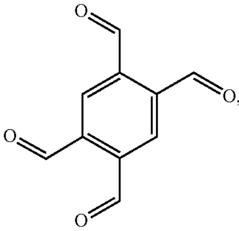
,

-continued

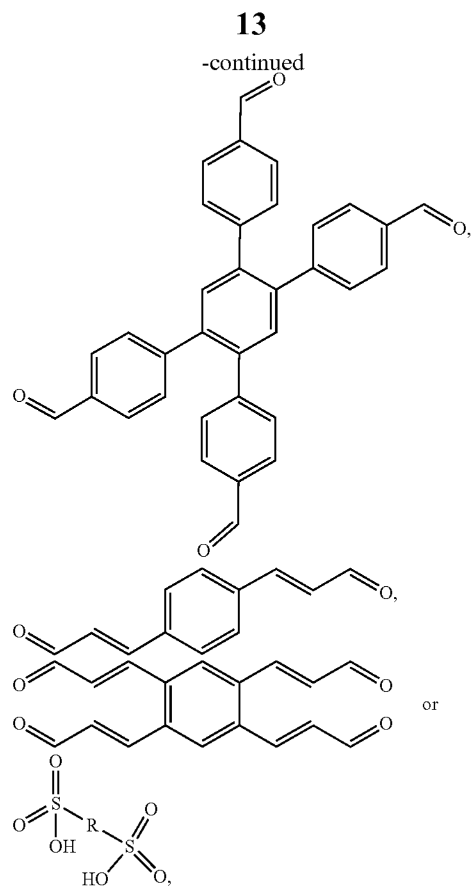

or wherein:

R is an alkylene, haloalkylene, cycloalkylene, heteroalkylene, haloheteroalkylene, cycloheteroalkylene, arylene, haloarylene, or haloheteroarylene group; and n is an integer from 1-20.

The photoresist layer 220 may include from about 0.1% to 10% by weight of crosslinker based upon the total weight of the polymer taken as 100% by weight. In some embodiments, the photoresist layer 220 includes from about 1% to about 5% by weight of crosslinker.

The photoresist may include a number of other optional ingredients as well. Typical optional ingredients include surfactants, amine bases, and adhesion promoters.

The photoresist layer 220 is formed by dispersing or dissolving the various components including polymer, the catalyst, and the crosslinker in a solvent to form a photoresist composition, and then applying the photoresist composition to the material layer 210 using, for example, spin coating. In some embodiments, the solvent is an organic solvent such as, ketones, alcohols, polyalcohols, ethers, glycol ethers, cyclic ethers, aromatic hydrocarbons, esters, propionates, lactates, lactic esters, alkylene glycol monoalkyl ethers, alkyl lactates, alkyl alkoxypropionates, cyclic lactones, monoketone compounds that contain a ring, alkylene carbonates, alkyl alkoxyacetate, alkyl pyruvates, lactate esters, ethylene glycol alkyl ether acetates, diethylene glycols, propylene glycol alkyl ether acetates, alkylene glycol alkyl ether esters, alkylene glycol monoalkyl esters, combinations thereof, or the like.

Specific examples of solvents that can be used in the photoresist composition include acetone, methanol, ethanol, propanol, isopropanol (IPA), n-butanol, toluene, xylene, 4-hydroxy-4-methyl-2-pentatone, tetrahydrofuran (THF), methyl ethyl ketone, cyclohexanone (CHN), methyl isoamyl ketone, 2-heptanone (MAK), ethylene glycol, 1-ethoxy-2-propanol, methyl isobutyl carbinol (MIBC), ethylene glycol monoacetate, ethylene glycol dimethyl ether, ethylene glycol dimethyl ether, ethylene glycol methylethyl ether, ethylene glycol monoethyl ether, methyl cellosolve acetate, ethyl cellosolve acetate, diethylene glycol, diethylene glycol monoacetate, diethylene glycol monomethyl ether, diethylene glycol diethyl ether, diethylene glycol dimethyl ether, diethylene glycol ethylmethyl ether, diethethylene glycol monoethyl ether, diethylene glycol monobutyl ether, ethyl 2-hydroxypropionate, methyl 2-hydroxy-2-methylpropionate, ethyl 2-hydroxy-2-methylpropionate, ethyl ethoxyacetate, ethyl hydroxyacetate, methyl 2-hydroxy-2-methylbutanate, methyl 3-methoxypropionate, ethyl 3-methoxypropionate, methyl 3-ethoxypropionate, ethyl 3-ethoxypropionate, methyl acetate, ethyl acetate, propyl acetate, n-butyl acetate (nBA), methyl lactate, ethyl lactate (EL), propyl lactate, butyl lactate, propylene glycol, propylene glycol monoacetate, propylene glycol monoethyl ether acetate, propylene glycol monomethyl ether acetate, propylene glycol monopropyl methyl ether acetate, propylene glycol monobutyl ether acetate, propylene glycol monobutyl ether acetate, propylene glycol monomethyl ether propionate, propylene glycol monoethyl ether propionate, propylene glycol methyl ether acetate, propylene glycol ethyl ether acetate, ethylene glycol monomethyl ether acetate, ethylene glycol monoethyl ether acetate, propylene glycol monomethyl ether, propylene glycol monoethyl ether, propylene glycol monopropyl ether, propylene glycol monobutyl ether, ethylene glycol monomethyl ether, ethylene glycol monoethyl ether, ethyl β-ethoxypropionate, methyl β-methoxypropionate, methyl β-ethoxypropionate, ethyl β-methoxypropionate, β-propiolactone, β-butyrolactone, γ-butyrolactone (GBL), α-methyl-γ-butyrolactone, β-methyl-γ-butyrolactone, γ-valerolactone, γ-caprolactone, γ-octanoic lactone, α-hydroxy-γ-butyrolactone, 2-butanone, 3-methylbutanone, pinacolone, 2-pentanone, 3-pentanone, 4-methyl-2-pentanone, 2-methyl-3-pentanone, 4,4-dimethyl-2-pentanone, 2,4-dimethyl-3-pentanone, 2,2,4,4-tetramethyl-3-pentanone, 2-hexanone, 3-hexanone, 5-methyl-3-hexanone, 3-heptanone, 4-heptanone, 2-methyl-3-heptanone, 5-methyl-3-heptanone, 2,6-dimethyl-4-heptanone, 2-octanone, 3-octanone, 2-nonanone, 3-nonanone, 5-nonanone, 2-decanone, 3-decanone, 4-decanone, 5-hexene-2-one, 3-pentene-2-one, cyclopentanone, 2-methylcyclopentanone, 3-methylcyclopentanone, 2,2-dimethylcyclopentanone, 2,4,4-trimethylcyclopentanone, cyclohexanone, 3-methylcyclohexanone, 4-methylcyclohexanone, 4-ethylcyclohexanone, 2,2-dimethylcyclohexanone, 2,6-dimethylcyclohexanone, 2,2,6-trimethylcyclohexanone, cycloheptanone, 2-methylcycloheptanone, 3-methyl cycloheptanone, propylene carbonate, vinylene carbonate, ethylene carbonate, butylene carbonate, acetate-2-methoxyethyl, acetate-2-ethoxyethyl, acetate-2-(2-ethoxyethoxy)ethyl, acetate-3-methoxy-3-methylbutyl, acetate-1-methoxy-2-propyl, dipropylene glycol, monomethyl ether, monoethylether, monopropylether, monobutylether, monophenylether, dipropylene glycol monoacetate, dioxane, methyl pyruvate, ethyl pyruvate, propyl pyruvate, methyl methoxypropionate, ethyl ethoxypropionate, n-methylpyrrolidone (NMP), 2-methoxyethyl ether (diglyme), ethylene glycol monomethyl ether, propylene glycol monomethyl ether, methyl propionate, ethyl propionate, ethyl ethoxy propionate, methylethyl ketone, cyclohexanone, 2-heptanone, cyclopentanone, cyclohexanone, ethyl 3-ethoxypropionate, propylene glycol methyl ether acetate (PGMEA), methylene cellosolve, 2-ethoxyethanol, N-methylformamide, N,N-dimethylformamide (DMF), N-methylformanilide, N-methyl acetamide, N,N-dimethylacetamide, dimethylsulfoxide, benzyl ethyl ether, dihexyl ether, acetonylacetone, isophorone, caproic acid, caprylic acid, 1-octanol, 1-nonanol, benzyl alcohol, benzyl acetate, ethyl benzoate, diethyl oxalate, diethyl maleate, phenyl cellosolve acetate, or the like.

The amount of solvent in the photoresist compositing may be from about 80% to about 99% by weight based upon the total weight of the composition as 100% by weight. In some embodiments, the amount of solvent in the photoresist compositing may be from about 95% to about 99% by weight.

Figure 2C:
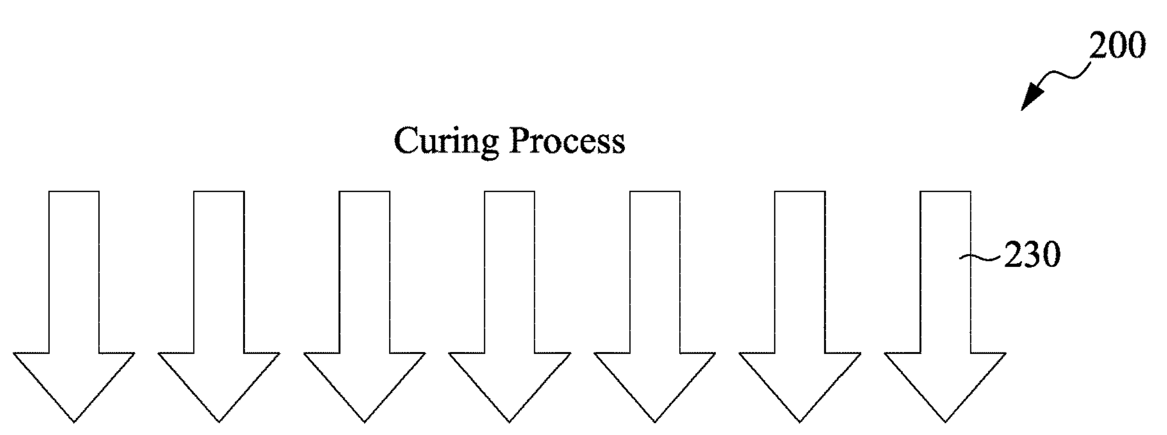
Figure 2C:
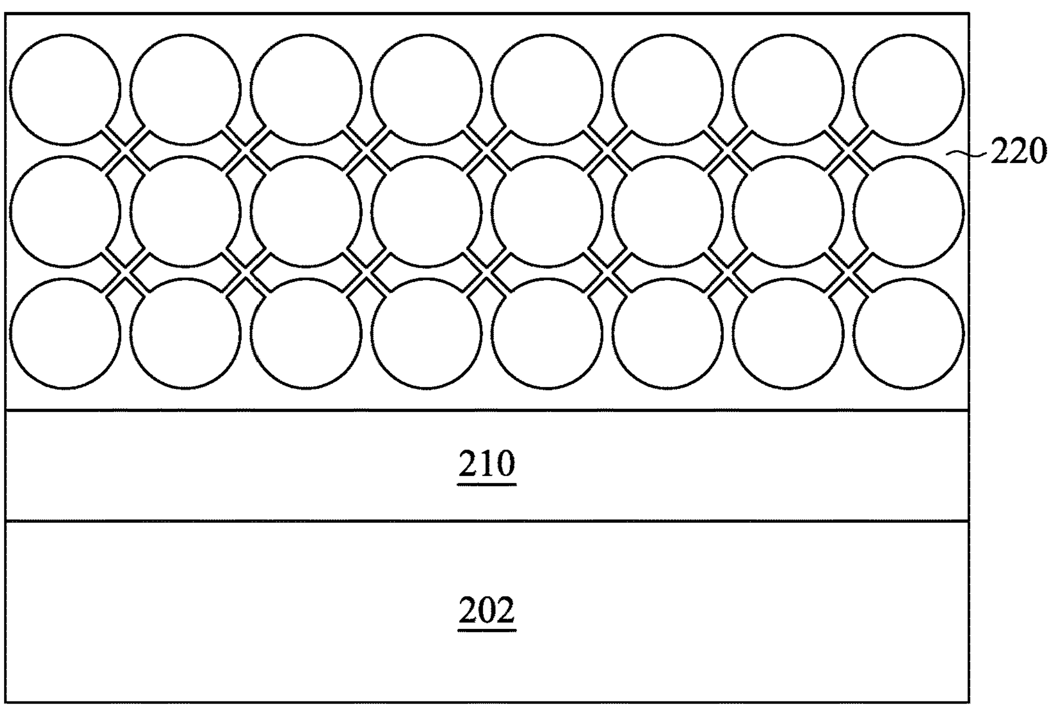

Referring to FIGS. 1 and 2C, the method 100 proceeds to operation 106, in which a curing process 230 is performed to the photoresist layer 220, in accordance with some embodiments. FIG. 2C is a cross-sectional view of the semiconductor structure 200 of FIG. 2B after performing the curing process 230 to the photoresist layer 220, in accordance with some embodiments.

During the curing process 230, the reactive group in the polymer and the crosslinkable functional groups in the crosslinker react with each other to crosslink the polymer, thereby increasing the mechanical strength and solvent resistance of the photoresist layer 220. After the photoresist layer 220 is cured, the photoresist layer 220 is substantially insoluble in typical photoresist solvents.

The curing process 230 may be a thermal curing process, a UV curing process or both. In some embodiments, the photoresist layer 220 is heated to a temperature that is above the crosslinking temperature to induce the crosslinking reaction between the polymer and the crosslinker. In some embodiments, the photoresist layer 220 is heated to a temperature from about 40° C. to about 250° C. In some embodiments, the photoresist layer 220 is heated to a temperature from about 60° C. to about 150° C. In some embodiments, the thermal curing also produces a weak acid to trigger the crosslinking reaction between the polymer and the crosslinker. In some embodiments, the photoresist layer 220 is irradiated by a UW light so that the crosslinking reaction between the polymer and the crosslinker is triggered by radicals generated by the UV light. In some embodiments, the photoresist layer 220 is irradiated by a UV light of a wavelength ranging from about 100 nm to about 400 nm. In some embodiments, the photoresist layer 220 is irradiated by a UV light of a wavelength ranging from about 170 nm to about 250 nm.

Figure 2D:
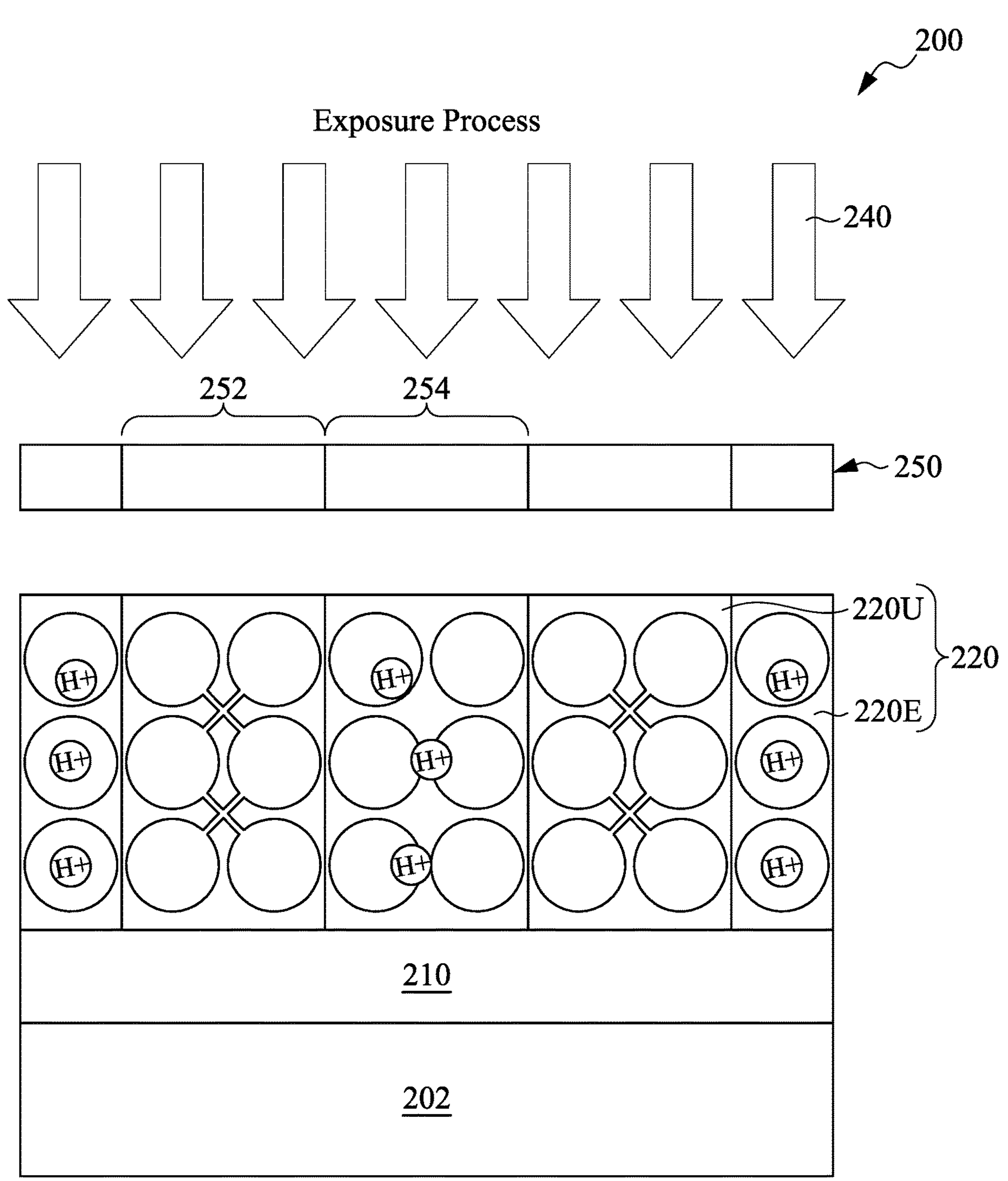

Referring to FIGS. 1 and 2D, the method 100 proceeds to operation 108, in which an exposure process 240 is performed to the photoresist layer 220, in accordance with some embodiments. FIG. 2D is a cross-sectional view of the semiconductor structure 200 of FIG. 2C after performing the exposure process 240 to the photoresist layer 220, in accordance with some embodiments.

During the exposure process 240, the photoresist layer 220 is exposed to a radiation from a light source through a photomask 250. In some embodiments, the photomask 250 is a transmissive mask. In some other embodiments, the photomask 250 is a reflective mask. The photomask 250 has a predefined pattern designed for an IC, based on a specification of the IC to be manufactured. The patterns of the photomask 250 correspond to patterns of materials that make up the various components of the IC device to be fabricated. For example, a portion of the IC design layout includes various IC features, such as an active region, gate electrode, source and drain, metal lines or vias of an interlayer interconnection, and openings for bonding pads, to be formed in the substrate 202 and/or the material layer 210 disposed on the substrate 202.

In some embodiments, the photomask 250 includes first regions 252 and second regions 254. In the first regions 252, the radiation is blocked by the photomask 250 to reach the photoresist layer 220, while in the second regions 254, the radiation is not blocked by the photomask 250 and can pass through the photomask 250 to reach the photoresist layer 220. As a result, portions of the photoresist layer 220 below the second regions 254 receive the radiation, referred to as exposed portions 220E, while portions of the photoresist layer 220 below the first regions 252 do not receive the radiation, referred to as unexposed portions 220U.

In some embodiments, the radiation is an EUV radiation (e.g., 13.5 nm). Alternatively, in some embodiments, the patterning radiation is a DUV radiation (e.g., from a 248 nm KrF excimer laser or a 193 nm ArF excimer laser), an X-ray radiation, an e-beam radiation, an ion beam radiation, or other suitable radiations. In some embodiments, the exposure process 240 is performed in a liquid (immersion lithography) or in a vacuum (e.g., for EUV lithography and e-beam lithography).

Upon exposure to the radiation, an acid is generated from the photoacid generator in the exposed portions 220E of the photoresist layer 220, and this acid de-crosslinks the crosslinked polymer in the exposed portions 220E of the photoresist layer 220. In some embodiments, the acid may break the bond that was formed between the reactive group in the polymer and the crosslinker in operation 106. The decrosslinking thus results in the formation of the same polymer originally present in the photoresist layer 220. In some other embodiments, the acid may cleave the cleavable group L, thereby causing the crosslinked polymer in the exposed portions 220E of the photoresist layer 220 to de-crosslink. Comparing to the crosslinked polymer, the de-crosslinked polymer has a lower molecular weight and a higher hydrophilicity. The exposed portions 220E of the photoresist layer 220 thus become soluble in a developer, while the unexposed portions 220U of the photoresist layer 220 remain insoluble and serve as a masking element for subsequent processes.

Figure 2E:
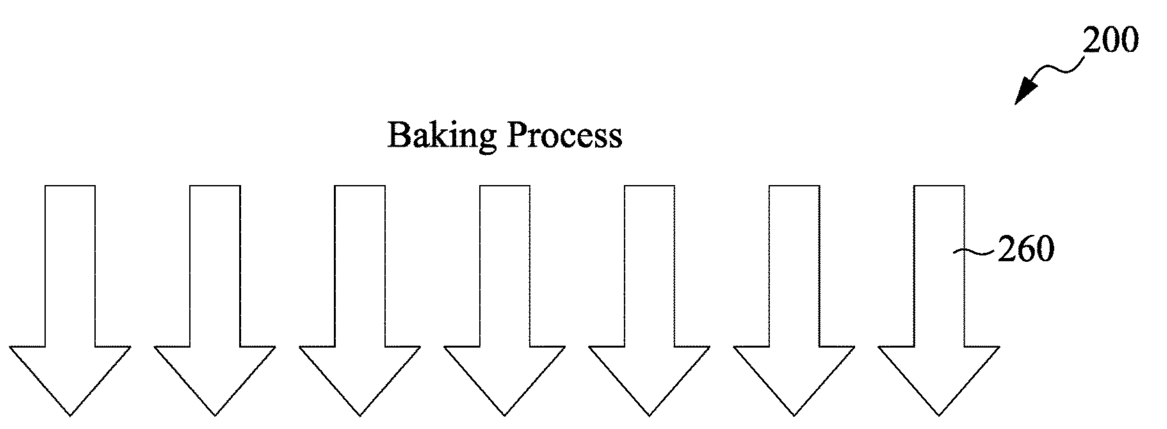
Figure 2E:
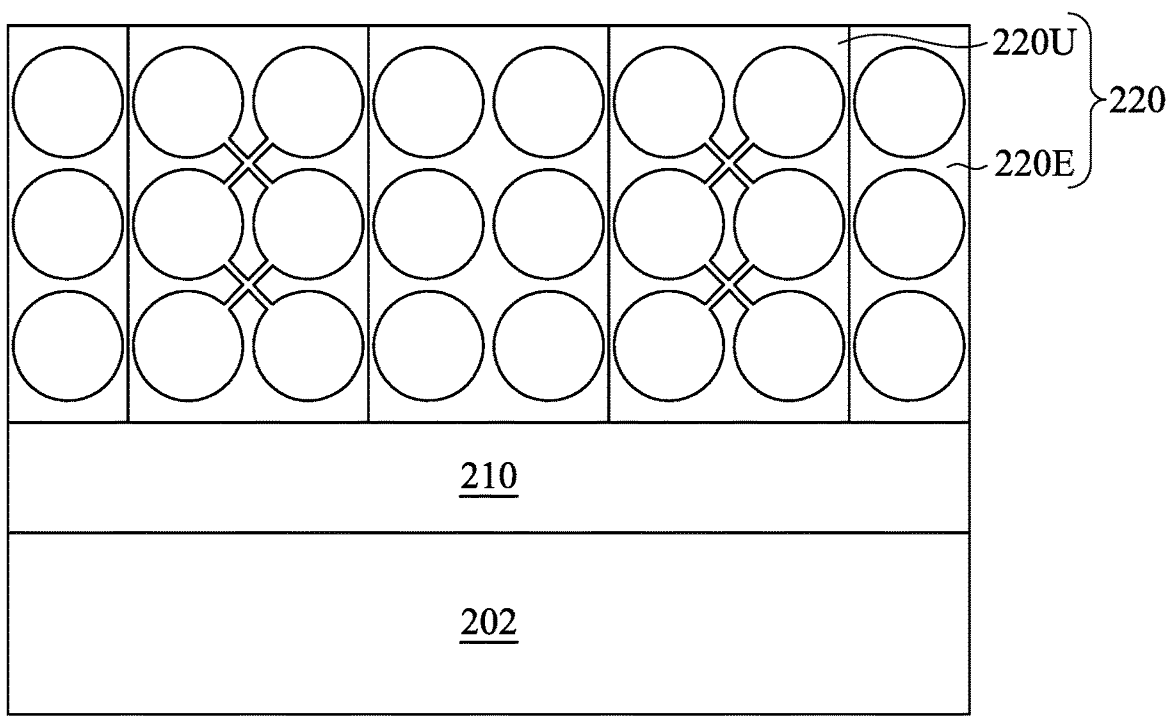

Referring to FIGS. 1 and 2E, the method 100 proceeds to operation 110, in which a baking process 260 is performed to the photoresist layer 220, in accordance with some embodiments. FIG. 2E is a cross-sectional view of the semiconductor structure 200 of FIG. 2D after performing the baking process 260, in accordance with some embodiments.

Since this baking process 260 is performed after the exposure process 240 that exposes the photoresist layer 220 to radiation, the baking process 260 may also be referred to as a post-exposure-baking (PEB) process. In some embodiments, the baking process 260 is performed at a temperature in a range from about 60° C. to about 150° C.

Figure 2F:
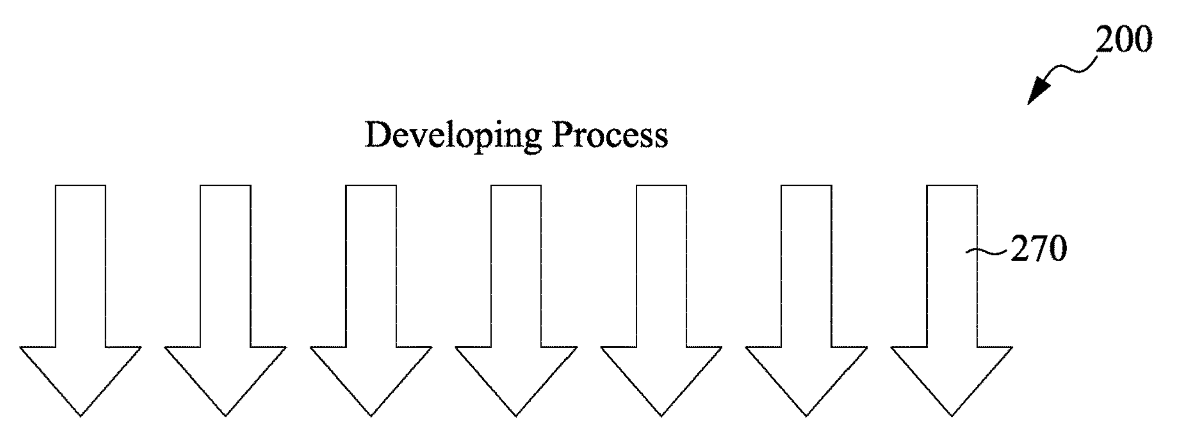
Figure 2F:
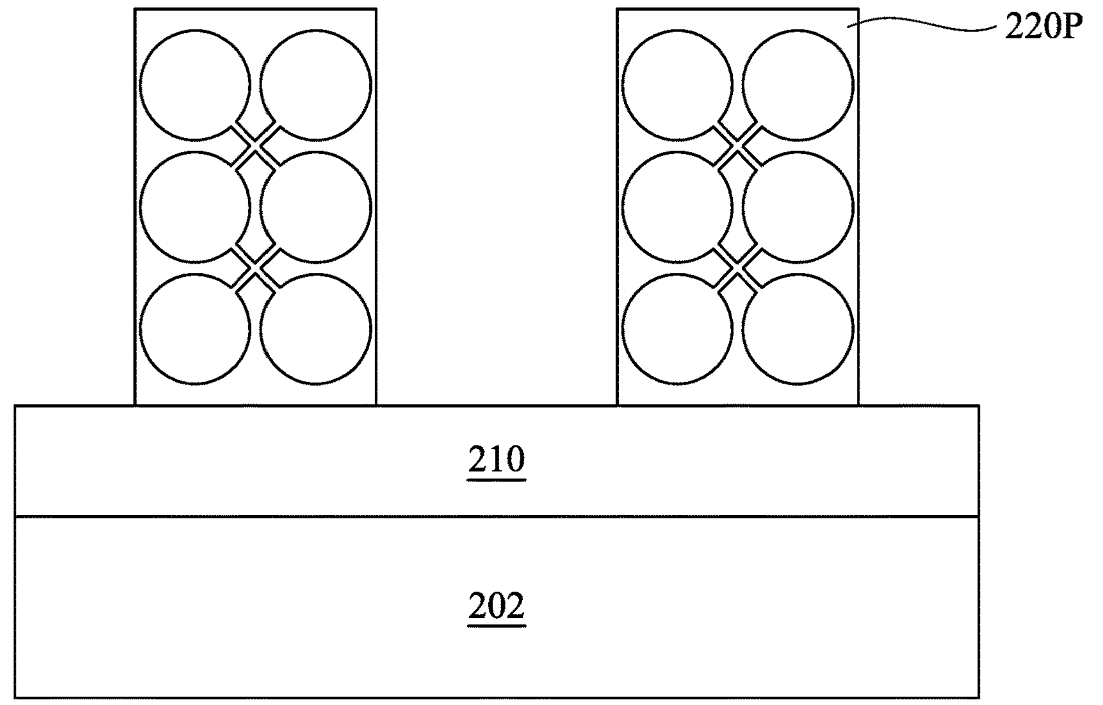

Referring to FIGS. 1 and 2F, the method 100 proceeds to operation 112, in which a developing process 270 is performed to the photoresist layer 220, in accordance with some embodiments. FIG. 2F is a cross-sectional view of the semiconductor structure 200 of FIG. 2E after performing the developing process 270 to the photoresist layer 220, in accordance with some embodiments.

The developing process 270 includes applying a developer to the photoresist layer 220. The developer removes the exposed portions 220E of the photoresist layer 220, leaving the unexposed portions 220U in the semiconductor structure 200. After the developing process, a patterned photoresist layer 220P is formed. The patterned photoresist layer 220P includes the exposed portions 220E of the photoresist layer 220.

The developer is selected so that it removes the exposed portions 220E of the photoresist layer 220. In some embodiments, a basic aqueous solution is used to remove the exposed portions 220E of the photoresist layer 220. Examples of basic aqueous solutions include tetramethylammonium hydroxide (TMAH), tetrabutylammonium hydroxide, sodium hydroxide, potassium hydroxide, sodium carbonate, sodium bicarbonate, sodium silicate, sodium metasilicate, aqueous ammonia, monomethylamine, dimethylamine, trimethylamine, monoethylamine, diethylamine, triethylamine, monoisopropylamine, diisopropylamine, triisopropylamine, monobutylamine, dibutylamine, monoethanolamine, diethanolamine, triethanolamine, dimethylaminoethanol, diethylaminoethanol, ammonia, caustic soda, caustic potash, sodium metasilicate, potassium metasilicate, sodium carbonate, tetraethylammonium hydroxide, combinations thereof, or the like.

In some embodiments, the developer is applied to the photoresist layer 220 using a spin coating process. In the spin coating process, the developer is applied to the photoresist layer 220 by a dispenser from above while the coated substrate 202 is rotated. In some embodiments, the developer is supplied at a rate of between about 5 ml/min and about 800 ml/min, while the coated substrate 202 is rotated at a speed of between about 100 rpm and about 2000 rpm. In some embodiments, the developer is at a temperature from about 10° C. to about 80° C. The development operation continues for between about 30 seconds to about 10 minutes in some embodiments.

While the spin coating operation is one suitable method for developing the photoresist layer 220 after exposure, it is intended to be illustrative and is not intended to limit the embodiment. Rather, any suitable development operations, including dip processes, puddle processes, and spray-on methods, may alternatively be used. All such development operations are included within the scope of the embodiments.

In the present disclosure, the increased solubility of the exposed portions 220E of the photoresist layer 220 in which the developer, due to the de-crosslinking of the crosslinked polymer in the exposed portions 220E, allows the exposed portions 220E to be easily removed by the developer. While in the unexposed portions 220U of the photoresist layer 220, the crosslinked polymer remains insoluble in the developer. The increased contrast between the crosslinked polymer in the unexposed portions 220U of the photoresist layer 220 and de-crosslinked polymer in the exposed portions 220E of the photoresist layer 220 improve the resist broken window and resist peeling window. Accordingly, improved resolution of the photoresist patterns can be achieved. As a result, the yield and reliability of the device are improved.

Figure 2G:
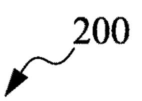
Figure 2G:
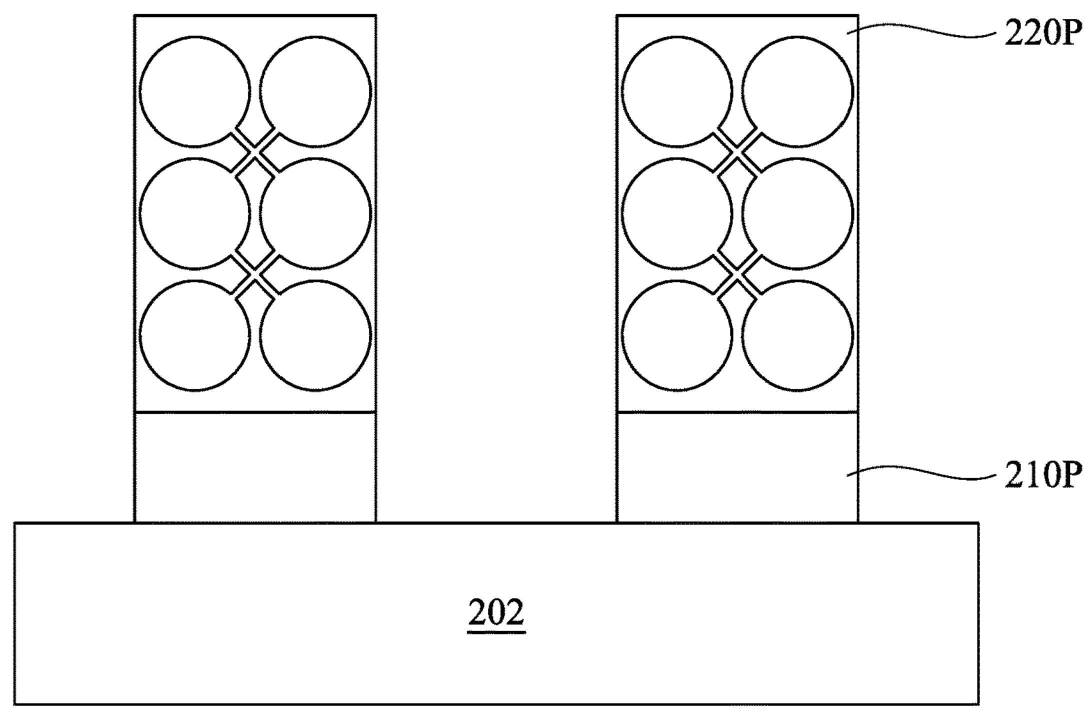

Referring to FIGS. 1 and 2G, the method 100 proceeds to operation 114, in which the material layer 210 is etched using the patterned photoresist layer 220P as an etch mask, in accordance with some embodiments. FIG. 2G is a cross-sectional view of the semiconductor structure 200 of FIG. 2F after etching the material layer 210 using the patterned photoresist layer 220P as an etch mask, in accordance with some embodiments.

As shown in FIG. 2G, the material layer 210 is patterned, using the patterned photoresist layer 220P as an etch mask, to form a patterned material layer 210P.

An etching process may be performed to transfer the pattern in the patterned photoresist layer 220P to the material layer 210. In some embodiments, the etching process employed is an anisotropic etch such as a dry etch although any suitable etch process may be utilized. In some embodiments, the dry etch is a reactive ion etch (RIE) or a plasma etch. In some embodiments, the dry etch is implemented by fluorine-containing gas (e.g., $CF_4$, $SF_6$, $CH_2F_2$, $CHF_3$, and/or $C_2F_6$), chlorine-containing gas (e.g., $Cl_2$, $CHCl_3$, $CCl_4$, and/or $BCl_3$), bromine-containing gas (e.g., HBr and/or $CHBr_3$), oxygen-containing gas, iodine-containing gas, other suitable gases and/or plasmas, or combinations thereof. In some embodiments, an oxygen plasma is performed to etch the material layer 210. In some embodiments, the anisotropic etch is performed at a temperature from about 250° C. to 450° C. for a duration from about 20 seconds to about 300 seconds.

If not completely consumed in the etching process, after formation of the patterned material layer 210P, the patterned photoresist layer 220P is removed, for example, by plasma ashing or wet stripping.

One aspect of this description relates to a method for forming a semiconductor structure. The method includes forming a photoresist layer over a substrate. The photoresist layer comprises a polymer, a photoacid initiator and a crosslinker containing at least two crosslinking sites. The method further includes performing a curing process to the photoresist layer, during which the crosslinker is crosslinked with the polymer to form a crosslinked polymer. The method further includes exposing the photoresist layer to a radiation, during which an acid produced from exposure of the photoacid generator de-crosslinks the crosslinked polymer in exposed portions of the photoresist layer. The method further includes removing the exposed portions of the photoresist layer to form a patterned photoresist layer.

Another aspect of this description relates to a method for forming a semiconductor structure. The method includes depositing a material layer over substrate; forming a photoresist layer over the material layer, wherein the photoresist layer comprises a polymer, a photoacid generator and a crosslinker, the crosslinker having the following structure:

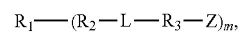

wherein: $R_1$ is alkylene, haloalkylene, cycloalkylene, heteroalkylene, haloheteroalkylene, cycloheteroalkylene, arylene, haloarylene or haloheteroarylene; $R_2$ and $R_3$, at each occurrence, are independently optional alkylene, haloalkylene, cycloalkylene, heteroalkylene, haloheteroalkylene, cycloheteroalkylene, arylene, haloarylene, or haloheteroarylene; L is an optional cleavable linker selected from the group consisting of ester, silyl ether, acetal, ketal, amide, imine, imide and carbamate; Z is a crosslinkable functional group selected from the group consisting of halide, hydroxyl, alkoxy, amine, thiol, ester, alkene, alkyne, epoxy, aziridine, oxetane, aldehyde, ketone, sulfonate and carboxylic acid; and m is an integer greater than 1. The method further includes forming a crosslinked polymer by initiating a crosslinking reaction between the crosslinker and the polymer; and exposing the photoresist layer to a radiation, during which an acid produced from exposure of the photoacid generator de-crosslinks the crosslinked polymer in exposed portions of the photoresist layer. The method further includes removing the exposed portions of the photoresist layer to form a patterned photoresist layer. The method further includes etching the material layer using the patterned photoresist layer as an etch mask.

Still another aspect of this description relates to a method for forming a semiconductor structure. The method includes forming a photoresist composition comprising a polymer, a photoacid generator, a crosslinker and a solvent. The polymer includes at least one reactive group, and the crosslinker comprises two or more crosslinkable functional groups each of which is coupled to a cleavable linker. The two or more crosslinkable functional groups are capable of crosslinking with the at least one reactive group of the polymer, and the cleavable linker is capable of being decomposed under an acidic condition of pH 1-2. The method further includes applying the photoresist composition to a substrate to form a photoresist layer thereon. The method further includes curing the photoresist layer. The curing causes the crosslinking reaction between the crosslinker and the polymer, thereby forming a crosslinked polymer. The method further includes exposing the photoresist layer to a radiation, during which an acid produced from exposure of the photoacid generator cleaves a bond of the cleavable linker, thereby de-crosslinking the crosslinked polymer in exposed portions of the photoresist layer. The method further includes removing the exposed portions of the photoresist layer to form a patterned photoresist layer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A method of forming a semiconductor structure, comprising:

forming a photoresist layer over a substrate, wherein the photoresist layer comprises a polymer, a photoacid initiator and a crosslinker, the crosslinker having one of the following structures:

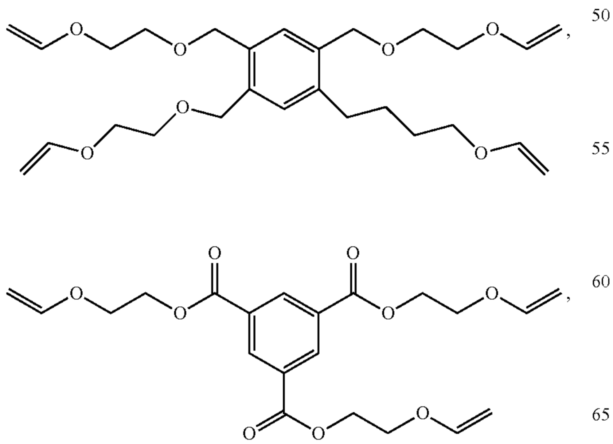

-continued

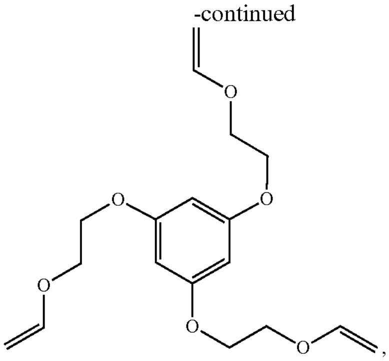

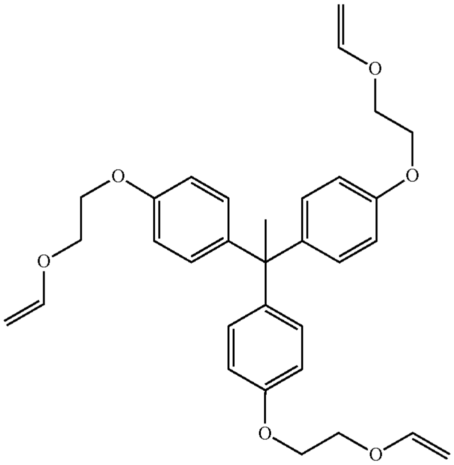

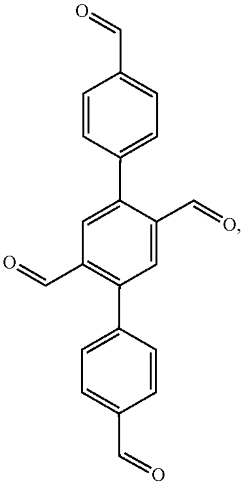

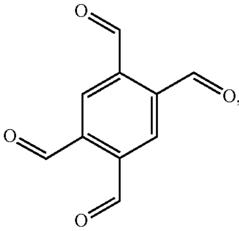

-continued

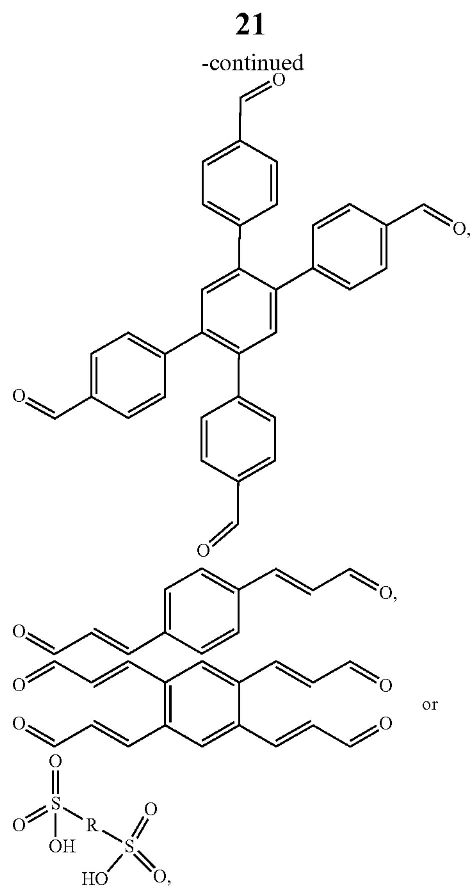

or wherein R is alkylene, haloalkylene, cycloalkylene, heteroalkylene, haloheteroalkylene, cycloheteroalkylene, arylene, haloarylene, or haloheteroarylene;

performing a curing process to the photoresist layer, wherein the crosslinker is crosslinked with the polymer to form a crosslinked polymer;

exposing the photoresist layer to a radiation, wherein an acid produced from exposure of a photoacid generator de-crosslinks the crosslinked polymer in exposed portions of the photoresist layer; and removing the exposed portions of the photoresist layer to form a patterned photoresist layer.

2. The method of claim 1, wherein the polymer comprises a reactive group capable of reacting with the crosslinker, the reactive group selected from the group consisting of a hydroxyl, alkoxy, amine, thiol, ester, alkene, alkyne, epoxy, aziridine, oxetane, aldehyde, ketone and carboxylic acid group.

3. The method of claim 1, wherein the de-crosslink of the crosslinked polymer is carried out under an acidic conduction with a pH of 1-3.

4. The method of claim 1, wherein the curing process is a thermal curing process performed at a temperature ranging from about 60° C. to about 150° C.

5. The method of claim 1, wherein the curing process is a thermal curing process that generates a weak acid having a pH of 4-6, wherein the weak acid induces the crosslinking of the crosslinker and the polymer.

6. The method of claim 1, wherein the curing process is an ultraviolet (UV) curing process performed by illuminating the photoresist layer with a UV light.

7. The method of claim 1, further comprising depositing a material layer over the substrate prior to forming the photoresist layer.

8. The method of claim 7, further comprising etching the material layer to transfer a pattern in the patterned photoresist layer to the material layer.

9. A method of forming a semiconductor structure, comprising:

depositing a material layer over a substrate;

forming a photoresist layer over the material layer, wherein the photoresist layer comprises a polymer, a photoacid generator and a crosslinker, the crosslinker having the following structure:

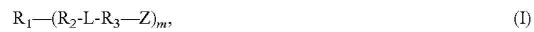

$R_1—(R_2\text{-}L\text{-}R_3—Z)_m$, (I)

wherein:

$R_1$ is alkylene, haloalkylene, cycloalkylene, heteroalkylene, haloheteroalkylene, cycloheteroalkylene, arylene, haloarylene or haloheteroarylene;

$R_2$ and $R_3$, at each occurrence, are independently optional alkylene, haloalkylene, cycloalkylene, heteroalkylene, haloheteroalkylene, cycloheteroalkylene, arylene, haloarylene, or haloheteroarylene;

L is an optional cleavable linker selected from the group consisting of ester, silyl ether, acetal, ketal, amide, imine, imide and carbamate;

Z is a crosslinkable functional group selected from the group consisting of aldehyde and sulfonic acid; and m is an integer greater than 1;

forming a crosslinked polymer by initiating a crosslinking reaction between the crosslinker and the polymer;

exposing the photoresist layer to a radiation, wherein an acid produced from exposure of the photoacid generator de-crosslinks the crosslinked polymer in exposed portions of the photoresist layer;

removing the exposed portions of the photoresist layer to form a patterned photoresist layer; and etching the material layer using the patterned photoresist layer as an etch mask.

10. The method of claim 9, wherein the crosslinker has one of the following structures:

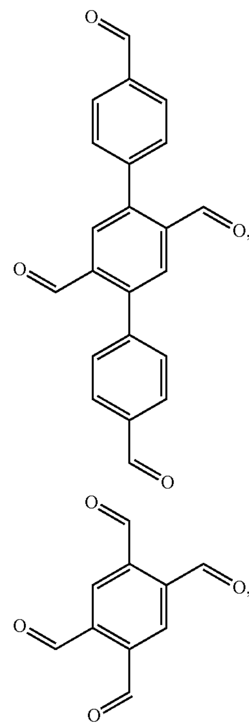

-continued

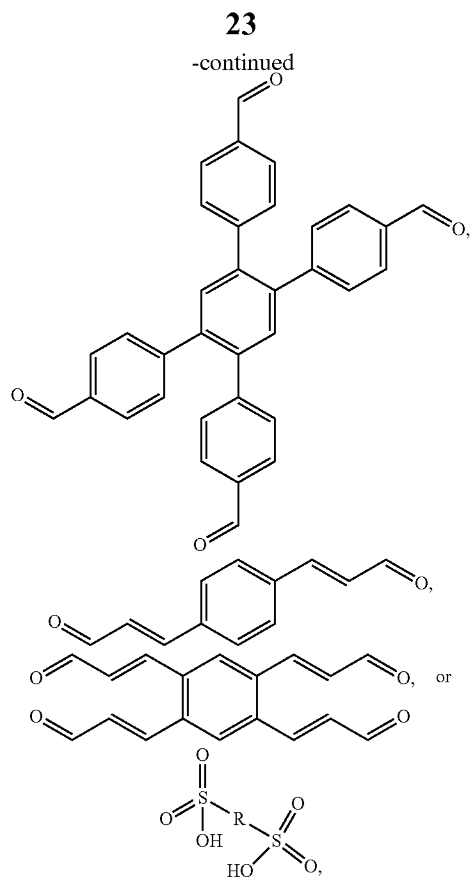

or wherein R is alkylene, haloalkylene, cycloalkylene, heteroalkylene, haloheteroalkylene, cycloheteroalkylene, arylene, haloarylene, or haloheteroarylene.

11. The method of claim 9, wherein the material layer is a low-k dielectric layer.

12. The method of claim 9, wherein forming the cross-linked polymer comprises heating the photoresist layer at a temperature ranging from about 60° C. to about 150° C.

13. The method of claim 9, wherein forming the cross-linked polymer comprises heating the photoresist layer to generate a weak acid having a pH of 4-6, wherein the weak acid initiates the crosslinking reaction of the crosslinker and the polymer.

14. The method of claim 9, wherein forming the cross-linked polymer comprises illuminating the photoresist layer with a UV light.

15. A method of forming a semiconductor structure, comprising:

forming a photoresist composition comprising a polymer, a photoacid generator, a crosslinker and a solvent, wherein the polymer comprises at least one reactive group and the crosslinker comprises two or more crosslinkable functional groups capable of crosslinking with the at least one reactive group of the polymer, wherein the crosslinker has one of the following structures:

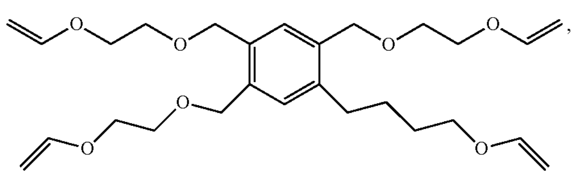

-continued

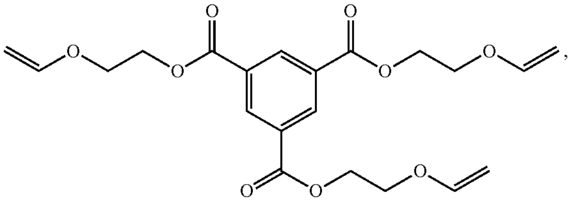

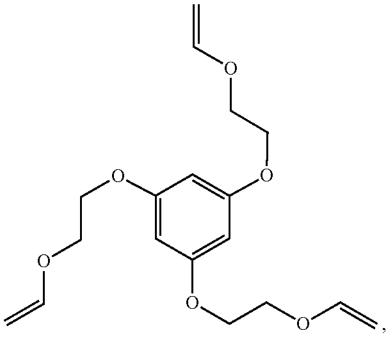

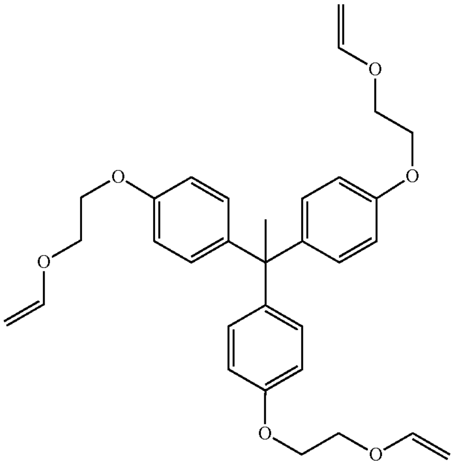

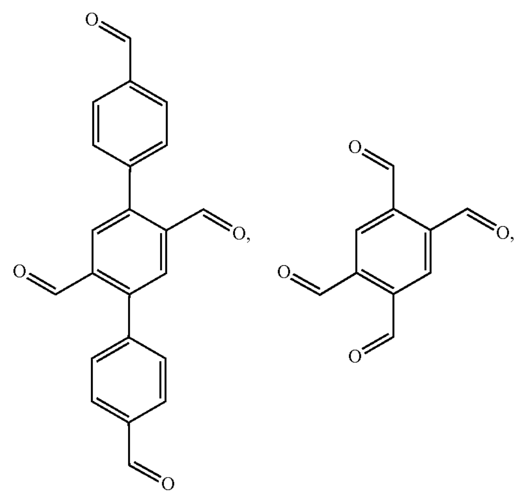

-continued

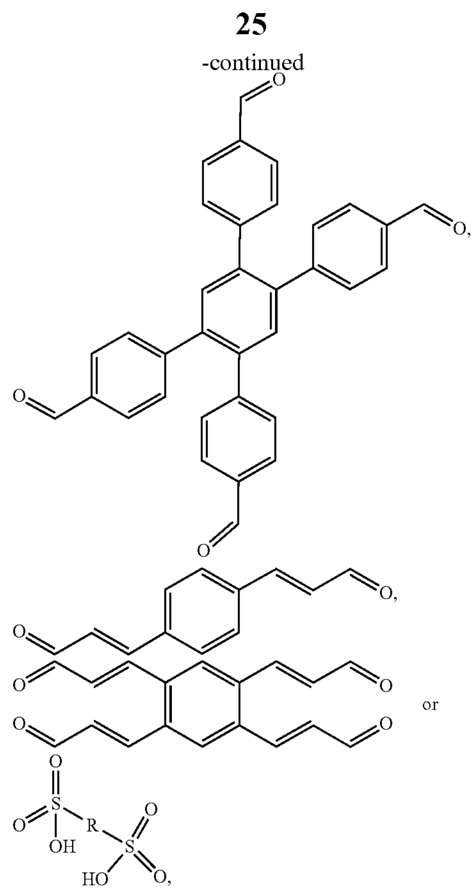

or wherein R is alkylene, haloalkylene, cycloalkylene, heteroalkylene, haloheteroalkylene, cycloheteroalkylene, arylene, haloarylene, or haloheteroarylene;

applying the photoresist composition to a material layer over a substrate to form a photoresist layer thereon;

curing the photoresist layer, wherein the curing causes the crosslinking reaction between the crosslinker and the polymer, thereby forming a crosslinked polymer;

exposing the photoresist layer to a radiation, wherein an acid produced from exposure of the photoacid generator de-crosslinks the crosslinked polymer in exposed portions of the photoresist layer; and removing the exposed portions of the photoresist layer to form a patterned photoresist layer.

16. The method of claim 15, wherein unexposed portions of the photoresist layer comprise the crosslinked polymer after exposing the photoresist layer to the radiation.

17. The method of claim 15, wherein curing the photoresist layer is performed at a curing temperature above a crosslinking temperature of the crosslinker.

18. The method of claim 17, wherein the curing temperature ranges from about 60° C. to about 150° C.

19. The method of claim 15, wherein the polymer comprises a polyacrylate, polymethacrylate, poly (hydroxy styrene) (PHS), polyester, polycarbonate, polyamic acid, poly (styrene)-co-maleic anhydride (COMA), a mixture thereof or a copolymer thereof.

20. The method of claim 1, wherein removing the exposed portions of the photoresist layer comprises applying a basic aqueous solution to the photoresist layer.

* * * * *